(12) United States Patent
Fusco

(10) Patent No.: US 7,078,050 B2
(45) Date of Patent: Jul. 18, 2006

(54) COMPOSITION FOR TOPICAL TREATMENT

(76) Inventor: Normajean Fusco, P. O. Box 180, Unionville, NY (US) 10988

( * ) Notice: Subject to any disclaimer, the term of this patent is extended or adjusted under 35 U.S.C. 154(b) by 94 days.

(21) Appl. No.: 10/971,908

(22) Filed: Oct. 25, 2004

(65) Prior Publication Data
US 2005/0053595 A1    Mar. 10, 2005

(51) Int. Cl.
- A61K 7/32 (2006.01)
- A61K 35/78 (2006.01)
- A61K 38/46 (2006.01)
- A61K 31/74 (2006.01)
- A61K 36/28 (2006.01)

(52) U.S. Cl. ............ 424/401; 424/74; 424/78.03; 424/78.07; 424/78.12; 424/94.6; 424/404; 424/725; 424/764; 424/769

(58) Field of Classification Search ............ 424/401, 424/74, 78.03, 78.07, 78.12, 94.6, 404, 725, 424/764, 769
See application file for complete search history.

(56) References Cited

U.S. PATENT DOCUMENTS

| | | | | |
|---|---|---|---|---|
| 5,879,684 A | * | 3/1999 | Fox | 424/401 |
| 5,997,893 A | * | 12/1999 | Jampani et al. | 424/405 |
| 6,022,551 A | * | 2/2000 | Jampani et al. | 424/405 |
| 6,022,565 A | * | 2/2000 | Albert et al. | 424/642 |
| 6,528,070 B1 | * | 3/2003 | Bratescu et al. | 424/401 |
| 2004/0161435 A1 | * | 8/2004 | Gupta | 424/401 |
| 2005/0084471 A1 | * | 4/2005 | Andrews et al. | 424/70.31 |
| 2005/0249763 A1 | * | 11/2005 | Legendre et al. | 424/401 |

* cited by examiner

Primary Examiner—Herbert J. Lilling
(74) Attorney, Agent, or Firm—Charles E Temko

(57) ABSTRACT

A white cream bacteriostat and fungicide capable of serving as a vehicle for additional medicaments. Also disclosed is a method for blending the ingredients, some of which are not readily compatible with each other.

3 Claims, No Drawings

COMPOSITION FOR TOPICAL TREATMENT

RELATED APPLICATION

Reference is made to my copending non-provisional application Ser. No. 09/323,282 filed Jun. 1, 1999, to which a claim of priority is made.

BACKGROUND OF THE INVENTION

This invention relates generally to compositions for treatment of the skin, and more particularly to an improved multi-purpose topically applied medicament composition suitable for treatment of a variety of acute dermal as well as subcutaneous conditions. The composition may be combined with a variety of other medicaments, wherein it serves as a vehicle for application.

While many dermal conditions are the result of internal body chemistry, and require the services of a medical provider, many relatively simple conditions may often be treated at home using non-prescription type remedies. Typical are such conditions as teenage acne, itching, swelling, as well as rashes caused by bacterial and microbial conditions. Individual remedies are known in the art for treating these conditions. However, the bulk of such remedies are only moderately effective in treating specific problems, and often are very slow acting.

The most common forms of bacteria and fungus which are the cause of most irritations are *Staphylococcus aureus* (ATCC 6538); *Pseudomonas aeruginosa* (ATCC 9027); and *E. coli* (ATCC 8739). Common forms of fungi include *Aspergillus niger* (ATCC 16404); and *Candida albicans* (ATCC 10231).

SUMMARY OF THE INVENTION

Briefly stated, the invention contemplates the provision of a single medicament capable of treating each of the above micro-bacterium and fungi, using a combination of ingredients in specific proportions in a base cream-type vehicle, suitable for treating a wide variety of skin problems. It also serves as a base vehicle in which additional ingredients may combine for specific known conditions. Although none of the ingredients employed are capable of substantially instant neutralization of such irritants, I have found that the disclosed composition passes U.S.P. xx iii (51) antimicrobial preservative effectiveness testing.

DETAILED DESCRIPTION OF THE DISCLOSED EMBODIMENT

In the disclosed embodiment, parts are by weight.

EXAMPLE 1

| | |
|---|---|
| Water purified (D.I.) | 81.95 |
| Cetyl Stearyl Alcohol (Promulgen D and Ceteareth-20)- Amerchol-Dow, Chicago, IL | 4.5 |
| Octyl Dodecanol (Eutonol G) - Sufactants, Inc., South Plainfield, NJ | 3.3 |
| Cetyl Alcohol NF (Cetal ™) - Haarman & Reimer GmbH, Springfield, NJ | 1.0 |
| Stearic Acid (Emersol 132) - Monson, Lewiston, ME | .4 |
| Polydimethyl Siloxane (liquid) (200 ® Fluid, 100 CS)- Dow Corning | .15 |
| Carbomer 934 (Carboxy Polymethylene Powder) Carbopol 934P ™, B. F. Goodrich, Cleveland, Ohio | .25 |
| Triethanolamine - Union Carbide | .5 |
| Menthyl Lactate - Haarman & Reimer, GmbH, Springfield, NJ | 4.5 |
| GERMABEN II (Liquid) - Sutton Laboratories, Chatham, New Jersey) | 1.0 |
| Bisabolol (BASF) | .30 |
| Chamomile (water extract) - Carrubba | .30 |
| Hamamelis Virginiana (Witch Hazel) - Carrubba | .30 |
| Corn Starch (Dry Flo AF Pure) (28-1855) National Starch | .30 |
| Lipase (Novo Nordisk A/S, Bagsuaerd, Denmark) | .10 |

Several of the ingredients are not readily compatible with each other, and require a careful mixing sequence. However, when preparation is completed, the composition is stable at room temperature.

Beginning in a first tank, the water is heated to 70–72 degrees C. at which point the Carbomer is carefully sifted and stirred with a high RPM mixer. Circulation is kept continuous using a high speed gear pump.

In a second tank, the Menthol Lactate in crystal form is heated in a closed container (double boiler) and raised to a temperature of approximately 70 degrees C., where it is maintained for at least two hours.

In a third tank, the Cetyl Alcohol, Octyl Dodecanol, Cetyl Stearyl Alcohol, Stearic Acid, and Polydimethysiloxane are heated and melted at a temperature ranging from 70–75 degrees C., which is maintained while the starch is slowly added. When the starch is circulated and mixed evenly in the third tank, and after at least one hour of stirring in the first tank, the contents of the third tank are added to the first tank where they are maintained at 70–72 degrees C. This process will ensure a very even consistency.

As the second tank contents melt from solid crystal to liquid, the Triethanolamine is separately heated in a fourth container to a degree just enough to maintain liquidity, which is about 70 degrees C.

The contents of the first and third tank are now at a very slurried consistency, and maintained at 70 degrees C., and are now thoroughly admixed. When the Triethanolamine is liquid, it is added at this temperature, which must be maintained, and all forms of circulation and mixing which include a selectively operable gear pump, a sweep mix agitator, and a paddle stirrer of all three tanks must be maintained as the contents will start to thicken instantly if the temperature falls, after which the mixture will become lumpy. Next, the GERMABEN II is added slowly to the first tank and the temperature is dropped about 5 degrees C. to 65 degrees C., at which point (and no cooler) the Menthol Lactate is added which is hot and liquid at about 70 degrees C. If this operation is performed at any other substantially different temperature, it will cause the Menthol Lactate to crystalize within the formula. After the Menthol Lactate circulates for at least fifteen to twenty minutes, the temperature controls are dropped and the contents of the first tank start to slowly cool. When the mixture reaches about 40 degrees C., the Chamomile, Bisabolol, and Hamamelis are added to the first tank with continued circulation and stirring. When all of the above ingredients are incorporated, the Lipase, which is stored at 1 degree C. is added, and circulation continued for approximately forty minutes before placing the composition in a holding tank. At this point, the composition is a white easily spreadable cream. It may be further admixed with additional medicaments for treatment of specific problems, or the composition may be used alone as a bacteriostat and fungicide. Typical additives are triclosan, to form a cleansing, manicure and pedicure lotion; benzyl peroxide, for treatment of blemishes; salicylic acid, for treatment of blemishes, and to form an after shave preparation; and SPF 15 to form a sunscreen. Triclosan is available from Jeen International-Corp., Fairfield, N.J., and consists of 2,4,4'-Trichloro-2'-Hydroxy Diphenyl Ether.

To provide for SPF 15, depending upon strength desired, zinc oxide and titanium dioxide (Escalol 567™ and Escalol 557™, available from Universal Preserve-a-Cam, Inc., South Edison, N.J.). are added.

A useful foot balm is provided by adding Golden Seal (hydratisis canadensis) available as a water extract from Carrubba.

When used as a bacteriostat and fungicide, it produces a substantial effect within one to two minutes.

GERMABEN II is a mixture comprised of diazolindinyl urea (about 30%); methyl paraben (about 11%); propyl paraben (about 3%), and propylene glycol (about 56%).

I wish it to be understood that I do not consider the invention to be limited to the exact quantities of ingredients specified, for obvious modifications will occur to those skilled in the art to which the invention pertains.

I claim:

1. A bacteriostat and antimicrobial vehicle for topical application comprising approximately, by weight, of:

| | |
|---|---|
| Water purified (D.I.) | 81.95 |
| Cetyl Stearyl Alcohol | 4.5 |
| Octyl Dodecanol | 3.3 |
| Cetyl Alcohol | 1.0 |
| Stearic Acid | .4 |
| Polydimethysiloxane | .15 |
| Carboxy Polymethylene Powder | .25 |
| Triethanolamine | .5 |
| Menthol Lactate | 4.5 |
| An anti-microbial mixture comprised of: diazolindinyl urea (about 30%) methyl paraben (about 11%) propyl paraben (about 3%), and propylene glycol (about 56%) | 1.0 |
| Bisabolol | .30 |
| Chamomile (Water extract) | .30 |
| Hamamelis (Witch Hazel) | .30 |
| Starch (Powder) | .30 |
| Lipase | .10. |

2. The vehicle in accordance with claim 1 in combination with an active ingredient selected from the group consisting of:
   1. 2,4,4'-Trichloro-2'-Hydroxy Diphenyl Ether
   2. Benzyl Peroxide
   3. Salicylic Acid
   4. Zinc oxide and titanium dioxide
   5. Golden Seal (herbal water extract).

3. A method of preparation of a bacteriostat and antimicrobial vehicle comprising the steps of, in which parts are by weight:
   a) heating in a first container approximately 81.95 parts of water to approximately 70 degrees C., and sifting into the water approximately 0.25 parts Carboxy Polymethylene;
   b) heating in a second closed container approximately 4.5 parts Menthol Lactate to approximately 70 degrees C., and maintaining same for at least one hour;
   c) melting in a third container approximately 1.0 parts Cetyl Alcohol, 3.3 parts Octyl Dodecanol, 4.5 parts Cetyl Stearyl Alcohol, 0.15 parts Polydimethysiloxane, and maintaining same at between 70–75 degrees C.;
   d) adding approximately 0.30 parts Starch to the mixture of step (c);
   e) adding the mixture of step (c) to the mixture of step (a) while maintaining stirring;
   f) in a separate vessel, heating approximately 0.5 parts Triethanolamine sufficient to maintain liquidity, and adding the same to the mixture of steps (a) and (c);
   g) adding to the above mixture approximately 1.0 parts an antimicrobial mixture comprised of:
      diazolindinyl urea (about 30%)
      methyl paraben (about 11%)
      propyl paraben (about 3%), and
      propylene glycol (about 56%); and subsequently allowing the temperature of the mixture to drop to approximately 65 degrees C.;
   h) adding approximately 4.5 parts Menthol Lactate at a temperature above 65 degrees C. and continue to circulate for at least fifteen to twenty minutes;
   i) when the mixture reaches approximately 40 degrees C., adding 0.30 parts Chamomile (water extract), 0.30 parts Bisabolol, and approximately 3.0 parts Hamamelis; and
   j) while continuing to stir, add 0.10 parts Lipase, following which the mixture is allowed to further cool.

* * * * *